United States Patent [19]

Fischer

[11] 3,933,462
[45] Jan. 20, 1976

[54] MIXTURE OF SUBSTITUTED BENZOTHIADIAZINONES AND BENZONITRILES AS HERBICIDES

[75] Inventor: Adolf Fischer, Mutterstadt, Germany

[73] Assignee: BASF Aktiengesellschaft, Ludwigshafen Germany

[22] Filed: July 30, 1974

[21] Appl. No.: 493,116

Related U.S. Application Data

[62] Division of Ser. No. 343,629, March 22, 1973, Pat. No. 3,888,655.

[30] Foreign Application Priority Data

Apr. 13, 1972 Germany............................ 2217722

[52] U.S. Cl. ........................... 71/91; 71/105; 71/121
[51] Int. Cl.² ............................................... A01N 9/12
[58] Field of Search................................. 71/91, 105

[56] References Cited
UNITED STATES PATENTS

| | | | |
|---|---|---|---|
| 3,272,795 | 9/1966 | Heywood et al. | 71/105 |
| 3,397,054 | 8/1968 | Hart et al. | 71/105 |
| 3,462,258 | 8/1969 | Linden et al. | 71/105 |
| 3,592,626 | 7/1971 | Heywood et al. | 71/105 |
| 3,708,277 | 1/1973 | Zeidler et al. | 71/91 |

OTHER PUBLICATIONS

Fischer, "Herbicidal compositions", (1970), CA 74, No. 22060z, (1971).

*Primary Examiner*—Glennon H. Hollrah
*Attorney, Agent, or Firm*—Johnston, Keil, Thompson & Shurtleff

[57] ABSTRACT

Herbicide mixtures of
a. a compound of the formula

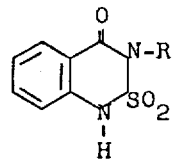

where R denotes lower alkyl of a maximum of 4 carbon atoms, or its salts, such as alkali metal, alkaline earth metal, ammonium, hydroxyalkylammonium, alkylammonium and hydrazine salts, e.g., salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and b. a compound of the formula

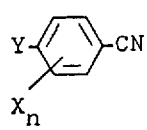

where Y denotes hydroxy or the radical
$-O-\underset{\underset{O}{\|}}{C}-(CH_2)_6-CH_3$, X denotes halogen and $n$ denotes the integer 2.

6 Claims, No Drawings

MIXTURE OF SUBSTITUTED BENZOTHIADIAZINONES AND BENZONITRILES AS HERBICIDES

RELATED APPLICATION

This application is a division application of my co-pending application Ser. No. 343,629, filed March 22, 1973 now U.S. Pat. No. 3,888,655.

The present invention relates to a herbicide comprising a composition of several active ingredients.

I have now found that a composition of
a. A compound of the formula

where R denotes lower alkyl of a maximum of 4 carbon atoms, or its salts, such as alkali metal, alkaline earth metal, ammonium, hydroxyalkylammonium, alkylammonium and hydrazine salts, e.g. salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and
b. a compound of the formula

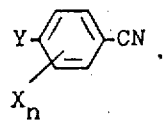

where Y denotes hydroxy or the radical

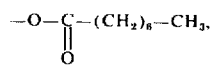

X denotes halogen and $n$ denotes the integer 2, have a herbicidal action superior to that of their individual components.

Active ingredients $a$ and $b$ may be applied in amounts of 0.5 to 5 kg per hectare.

The weight ratio of $a : b$ is from 5:1 to 1:5, preferably from 3:1 to 1:3.

The compositions of the invention are suitable for controlling unwanted plants, e.g. dicotyledonous seed weeds, monocotyledonous grassy seed weeds and Cyperaceae in crops such as cereals, rice, soybeans, Indian corn, potatoes, peas, and beans.

The compositions may be used pre- and/or postemergence.

The agents according to the invention may be used as solutions, emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

EXAMPLE 1

In the open the crop plants wheat (*Triticum aestivum*), barley (*Hordeum vulgare*), rye (*Secale cereale*) and lawn grass, and the unwanted plants wild mustard (*Sinapis arvensis*), hempnettle (*Galeopsis tetrahit*), catchweed bedstraw (*Galium aparine*), kochia (*Kochia scoparia*), red deadnettle (*Lamium purpureum*), gromwell (*Lithospermum officinale*), chamomile (*Matricaria chamomilla*), redroot pigweed (*Amaranthus retroflexus*) and common cocklebur (*Xanthium pensylvanicum*) are treated postemergence with the following amounts of the following individual active ingredients and compositions thereof:

I. 3,5-dibromo-4-hydroxybenzonitrile, 0.4 kg per hectare;
II. 3,5-diiodo-4-hydroxybenzonitrile, 0.3 kg per hectare;
III. 3,5-dibromo-4-octanoyloxybenzonitrile, 0.5 kg per hectare;
IV. 3-isopropyl-2,1,3-benzothiadiazinone-(4)-2,2-dioxide, 0.5 kg per hectare;
I + IV: 0.4 + 0.5 kg per hectare;
II + IV: 0.3 + 0.5 kg per hectare;
III + IV: 0.5 + 0.5 kg per hectare;

After 10 to 14 days it was ascertained that the compositions had a better herbicidal action than their individual components, combined with the same good crop plant compatibility.

The results are given below:

| Active ingredient kg/ha | I 0.4 | II 0.3 | III 0.5 | IV 0.5 | I + IV 0.4 + 0.5 | II + IV 0.3 + 0.5 | III + IV 0.5 + 0.5 |
|---|---|---|---|---|---|---|---|
| Triticum aestivum | 5 | 10 | 0 | 0 | 0 | 5 | 0 |
| Hordeum vulgare | 0 | 5 | 0 | 0 | 0 | 0 | 0 |
| Secale cereale | 0 | 5 | 0 | 0 | 0 | 0 | 0 |
| lawn grass | 0 | 0 | 0 | 0 | 0 | 0 | 0 |
| Sinapis arvensis | 30 | 35 | 15 | 25 | 80 | 90 | 70 |

-continued

| Active ingredient | I | II | III | IV | I + IV | II + IV | III + IV |
|---|---|---|---|---|---|---|---|
| kg/ha | 0.4 | 0.3 | 0.5 | 0.5 | 0.4 + 0.5 | 0.3 + 0.5 | 0.5 + 0.5 |
| Galeopsis tetrahit | 25 | 30 | 20 | 25 | 75 | 85 | 75 |
| Galium aparine | 20 | 30 | 15 | 35 | 90 | 100 | 85 |
| Kochia scoparia | 25 | 25 | 15 | 20 | 70 | 80 | 80 |
| Lamium purpureum | 30 | 40 | 25 | 10 | 80 | 90 | 90 |
| Lithospermum officinale | 25 | 30 | 20 | 25 | 75 | 90 | 85 |
| Matricaria chamomilla | 20 | 30 | 20 | 35 | 80 | 100 | 75 |
| Amaranthus retroflexus | 30 | 35 | 25 | 30 | 90 | 100 | 95 |
| Xanthium pensylvanicum | 20 | 25 | 20 | 40 | 85 | 95 | 90 |

0 = no damage
100 = complete destruction

EXAMPLE 2

In the open, various plants were treated at a growth height of 3 to 25 cm with the following amounts of the following active ingredients and compositions thereof as oil dispersions:

I. sodium salt of 3-isopropyl-2,1,3-benzothiadiazinone-(4)-2,2-dioxide, 0.15, 0.45, 0.75 and 0.9 kg/hectare;

II. dimethylamine salt of 3-isopropyl-2,1,3-benzothiadiazinone-(4)-2,2-dioxide, 0.15, 0.45, 0.75 and 0.9 kg/hectare;

III. diethanolamine salt of 3-isopropyl-2,1,3-benzothiadiazinone-(4)-2,2-dioxide, 0.15, 0.45, 0.75 and 0.9 kg/hectare;

IV. 3,5-dibromo-4-hydroxybenzaldoxime-O-(2',4'-dinitrophenyl)-ether, 0.15, 0.45, 0.75 and 0.9 kg/hectare;

V. 3,5-diiodo-4-hydroxybenzonitrile, 0.15, 0.45, 0.75 and 0.9 kg/hectare;

VI. 3,5-dibromo-4-hydroxybenzonitrile, 0.15, 0.45, 0.75 and 0.9 kg/hectare;

I + IV: 0.15 + 0.75; 0.75 + 0.15; 0.45 + 0.45 kg/ha;
I + V : 0.15 + 0.75; 0.75 + 0.15; 0.45 + 0.45 kg/ha;
I + VI: 0.15 + 0.75; 0.75 + 0.15; 0.45 + 0.45 kg/ha;
II + IV: 0.15 + 0.75; 0.75 + 0.15; 0.45 + 0.45 kg/ha;
II + V : 0.15 + 0.75; 0.75 + 0.15; 0.45 + 0.45 kg/ha;
II + VI: 0.15 + 0.75; 0.75 + 0.15; 0.45 + 0.45 kg/ha;
III + IV: 0.15 + 0.75; 0.75 + 0.15; 0.45 + 0.45 kg/ha;
III + V : 0.15 + 0.75; 0.75 + 0.15; 0.45 + 0.45 kg/ha;
III + VI: 0.15 + 0.75; 0.75 + 0.15; 0.45 + 0.45 kg/ha.

After 8 to 12 days it was ascertaineed that the compositions had a better herbicidal action than their individual components, combined with the same good crop plant compatibility.

The results are given below:

| Active ingredient | I | | | | II | | | | III | | | |
|---|---|---|---|---|---|---|---|---|---|---|---|---|
| kg/ha | 0.15 | 0.45 | 0.75 | 0.9 | 0.15 | 0.45 | 0.75 | 0.9 | 0.15 | 0.45 | 0.75 | 0.9 |
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 10 | 30 | 40 | 55 | 10 | 26 | 40 | 47 | 14 | 28 | 45 | 60 |
| Lamium amplexicaule | 0 | 10 | 15 | 23 | 0 | 9 | 20 | 35 | 3 | 10 | 25 | 32 |
| Stellaria media | 7 | 18 | 30 | 42 | 10 | 26 | 35 | 45 | 6 | 20 | 40 | 50 |

0 = no damage
100 = complete destruction

| Active ingredient | IV | | | | V | | | | VI | | | |
|---|---|---|---|---|---|---|---|---|---|---|---|---|
| kg/ha | 0.15 | 0.45 | 0.75 | 0.9 | 0.15 | 0.45 | 0.75 | 0.9 | 0.15 | 0.45 | 0.75 | 0.9 |
| Crop plants: | | | | | | | | | | | | |
| Triticum aestivum | 0 | 0 | 0 | 0 | 0 | 10 | 12 | 15 | 0 | 5 | 5 | 10 |
| Hordeum vulgare | 0 | 0 | 5 | 5 | 0 | 5 | 7 | 10 | 0 | 0 | 0 | 5 |
| Secale cereale | 0 | 0 | 0 | 5 | 0 | 6 | 10 | 15 | 0 | 0 | 0 | 7 |
| Unwanted plants: | | | | | | | | | | | | |
| Galium aparine | 5 | 15 | 20 | 30 | 14 | 35 | 54 | 74 | 11 | 20 | 30 | 48 |
| Lamium amplexicaule | 12 | 33 | 45 | 60 | 10 | 30 | 43 | 67 | 8 | 30 | 40 | 60 |
| Stellaria media | 7 | 22 | 30 | 48 | 10 | 25 | 37 | 58 | 7 | 20 | 31 | 50 |

0 = no damage
100 = complete destruction

| Active ingredient | I + IV | | | I + V | | |
|---|---|---|---|---|---|---|
| kg/ha | 0.15+0.75 | 0.75+0.15 | 0.45+0.45 | 0.15+0.75 | 0.75+0.15 | 0.45+0.45 |
| Crop plants: | | | | | | |
| Triticum aestivum | 0 | 0 | 0 | 12 | 0 | 0 |
| Hordeum vulgare | 5 | 0 | 0 | 7 | 0 | 5 |
| Secale cereale | 0 | 0 | 0 | 10 | 0 | 6 |
| Unwanted plants: | | | | | | |
| Galium aparine | 70 | 80 | 83 | 96 | 90 | 88 |
| Lamium amplexicaule | 90 | 68 | 80 | 78 | 65 | 82 |

-continued

| Active ingredient kg/ha | I + IV | | | I + V | | |
|---|---|---|---|---|---|---|
| | 0.15+0.75 | 0.75+0.15 | 0.45+0.45 | 0.15+0.75 | 0.75+0.15 | 0.45+0.45 |
| Stellaria media | 75 | 78 | 85 | 80 | 77 | 81 |

0 = no damage
100 = complete destruction

| Active ingredient kg/ha | I + VI | | | II + IV | | |
|---|---|---|---|---|---|---|
| | 0.15+0.75 | 0.75+0.15 | 0.45+0.45 | 0.15+0.75 | 0.75+0.15 | 0.45+0.45 |
| Crop plants: | | | | | | |
| Triticum aestivum | 5 | 0 | 5 | 0 | 0 | 0 |
| Hordeum vulgare | 0 | 0 | 0 | 5 | 0 | 0 |
| Secale cereale | 0 | 0 | 0 | | | |
| Unwanted plants: | | | | | | |
| Galium aparine | 76 | 90 | 87 | 68 | 82 | 80 |
| Lamium amplexicaule | 73 | 60 | 76 | 82 | 70 | 78 |
| Stellaria media | 75 | 73 | 80 | 80 | 79 | 90 |

0 = no damage
100 = complete destruction

| Active ingredient kg/ha | II + V | | | II + VI | | |
|---|---|---|---|---|---|---|
| | 0.15+0.75 | 0.75+0.15 | 0.45+0.45 | 0.15+0.75 | 0.75+0.15 | 0.45+0.45 |
| Crop plants: | | | | | | |
| Triticum aestivum | 12 | 0 | 10 | 5 | 0 | 5 |
| Hordeum vulgare | 7 | 0 | 5 | 0 | 0 | 0 |
| Secale cereale | 10 | 0 | 6 | 0 | 0 | 0 |
| Unwanted plants: | | | | | | |
| Galium aparine | 97 | 95 | 93 | 78 | 90 | 84 |
| Lamium amplexicaule | 80 | 67 | 75 | 74 | 66 | 73 |
| Stellaria media | 85 | 83 | 92 | 80 | 85 | 88 |

0 = no damage
100 = complete destruction

| Active ingredient kg/ha | III + IV | | | III + V | | |
|---|---|---|---|---|---|---|
| | 0.15+0.75 | 0.75+0.15 | 0.45+0.45 | 0.15+0.75 | 0.75+0.15 | 0.45+0.45 |
| Crop plants: | | | | | | |
| Triticum aestivum | 0 | 0 | 0 | 12 | 0 | 10 |
| Hordeum vulgare | 5 | 0 | 0 | 7 | 0 | 5 |
| Secale cereale | 0 | 0 | 0 | 10 | 0 | 6 |
| Unwanted plants: | | | | | | |
| Galium aparine | 67 | 83 | 80 | 100 | 97 | 95 |
| Lamium amplexicaule | 80 | 64 | 78 | 83 | 76 | 77 |
| Stellaria media | 74 | 76 | 82 | 80 | 93 | 84 |

0 = no damage
100 = complete destruction

| Active ingredient kg/ha | III + VI | | |
|---|---|---|---|
| | 0.15+0.75 | 0.75+0.15 | 0.45+0.45 |
| Crop plants: | | | |
| Triticum aestivum | 5 | 0 | 5 |
| Hordeum vulgare | 0 | 0 | 0 |
| Secale cereale | 0 | 0 | 0 |
| Unwanted plants: | | | |
| Galium aparine | 80 | 92 | 86 |
| Lamium amplexicaule | 75 | 70 | 78 |
| Stellaria media | 72 | 85 | 79 |

0 = no damage
100 = complete destruction

EXAMPLE 3

In the greenhouse, various plants were treated at a growth height of 4 to 27 cm with the following amounts of the following individual active ingredients and compositions thereof as dispersions:

I. 3-isopropyl-2,1,3-benzothiadiazinone-(4)-2,2-dioxide, 1.0, 1.5, 2.0 and 3.0 kg/ha;

II. 3,5-dibromo-4-hydroxybenzonitrile, 1.0, 1.5, 2.0 and 3.0 kg/ha;

III. 3,5-diiodo-4-hydroxybenzonitrile, 1.0, 1.5, 2.0 and 3.0 kg/ha;

IV. 3,5-dibromo-4-hydroxybenzaldoxime-O-(2',4'-dinitrophenyl)-ether, 1.0, 1.5, 2.0 and 3.0 kg/ha;

I + II : 2.0 + 1.0; 1.0 + 2.0; 1.0 + 1.0; and 1.5 + 1.5 kg/ha;

I + III : 2.0 + 1.0; 1.0 + 2.0; 1.0 + 1.0; and 1.5 + 1.5 kg/ha;

I + IV : 2.0 + 1.0; 1.0 + 2.0; 1.0 + 1.0; and 1.5 + 1.5 kg/ha;

compared with

V. 1-p-chlorophenyl-3,3-dimethylurea, 2.0 and 3.0 kg/ha; and

V + I: 2.0 + 1.0 kg/ha.

After 12 to 15 days it was ascertained that the compositions I + II, I + III and I + IV had a better crop plant compatibility than their individual components; active ingredient V; and composition V + I, combined with the same good herbicidal action. The results are given below:

| Active ingredient | I | | | | II | | | | III | | | |
|---|---|---|---|---|---|---|---|---|---|---|---|---|
| kg/ha | 1.0 | 1.5 | 2.0 | 3.0 | 1.0 | 1.5 | 2.0 | 3.0 | 1.0 | 1.5 | 2.0 | 3.0 |
| Crop plants: | | | | | | | | | | | | |
| Triticum aestivum | 0 | 0 | 0 | 0 | 10 | 12 | 15 | 20 | 15 | 18 | 20 | 30 |
| Hordeum vulgare | 0 | 0 | 0 | 0 | 5 | 6 | 8 | 10 | 10 | 15 | 18 | 26 |
| Secale cereale | 0 | 0 | 0 | 0 | 8 | 10 | 14 | 18 | 17 | 20 | 25 | 31 |
| Unwanted plants: | | | | | | | | | | | | |
| Galium aparine | 40 | 60 | 70 | 80 | 50 | 67 | 90 | 100 | 75 | 90 | 98 | 100 |
| Lamium amplexicaule | 40 | 50 | 60 | 70 | 60 | 70 | 85 | 100 | 70 | 80 | 94 | 100 |
| Stellaria media | 60 | 70 | 90 | 95 | 54 | 78 | 90 | 100 | 60 | 83 | 97 | 100 |

0 = no damage
100 = complete destruction

| Active ingredient | I + II | | | | I + III | | | |
|---|---|---|---|---|---|---|---|---|
| kg/ha | 2.0+1.0 | 1.0+2.0 | 1.0+1.0 | 1.5+1.5 | 2.0+1.0 | 1.0+2.0 | 1.0+1.0 | 1.5+1.5 |
| Crop plants: | | | | | | | | |
| Triticum aestivum | 10 | 15 | 10 | 12 | 15 | 20 | 15 | 18 |
| Hordeum vulgare | 5 | 8 | 5 | 6 | 10 | 18 | 10 | 15 |
| Secale cereale | 8 | 14 | 8 | 10 | 17 | 25 | 17 | 20 |
| Unwanted plants: | | | | | | | | |
| Galium aparine | 100 | 100 | 100 | 100 | 100 | 100 | 100 | 100 |
| Lamium amplexicaule | 100 | 100 | 100 | 100 | 100 | 100 | 100 | 100 |
| Stellaria media | 100 | 100 | 100 | 100 | 100 | 100 | 100 | 100 |

0 = no damage
100 = complete destruction

| Active ingredient | IV | | | | V | |
|---|---|---|---|---|---|---|
| kg/ha | 1.0 | 1.5 | 2.0 | 3.0 | 2.0 | 3.0 |
| Crop plants: | | | | | | |
| Triticum aestivum | 0 | 10 | 15 | 19 | 40 | 70 |
| Hordeum vulgare | 7 | 15 | 20 | 25 | 47 | 80 |
| Secale cereale | 6 | 10 | 12 | 18 | 56 | 95 |
| Unwanted plants: | | | | | | |
| Galium aparine | 30 | 45 | 60 | 100 | 90 | 95 |
| Lamium amplexicaule | 65 | 80 | 95 | 100 | 100 | 100 |
| Stellaria media | 50 | 70 | 93 | 100 | 100 | 100 |

0 = no damage
100 = complete destruction

| Active ingredient | I + IV | | | | I + V |
|---|---|---|---|---|---|
| kg/ha | 2.0+1.0 | 1.0+2.0 | 1.0+1.0 | 1.5+1.5 | 1.0+2.0 |
| Crop plants: | | | | | |
| Triticum aestivum | 0 | 15 | 0 | 10 | 40 |
| Hordeum vulgare | 7 | 20 | 7 | 15 | 47 |
| Secale cereale | 6 | 12 | 6 | 10 | 56 |
| Unwanted plants: | | | | | |
| Galium aparine | 100 | 100 | 100 | 100 | 100 |
| Lamium amplexicaule | 100 | 100 | 100 | 100 | 100 |
| Stellaria media | 100 | 100 | 100 | 100 | 100 |

0 = no damage
100 = complete destruction

I claim:

1. A herbicide composition comprising an inert carrier containing a herbicidally effective amount of a mixture of herbicides consisting essentially of a. a compound of the formula

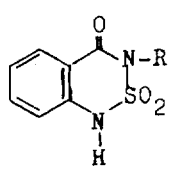

where R denotes lower alkyl of a maximum of 4 carbon atoms, or an alkali metal, ammonium, alkaline earth metal, lower alkyl ammonium, lower hydroxyalkylammonium or hydrazine salt thereof, and b. a compound of the formula

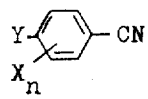

where Y denotes hydroxy or the radical

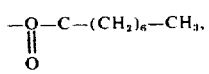

X denotes bromine or iodine and $n$ denotes the integer 2 in a weight ratio of $a$ to $b$ in the range of 5:1 to 1:5.

2. A herbicide composition as claimed in cliam 1 wherein the weight ratio of $a$ to $b$ is 3:1 to 1:3.

3. A herbicide composition as claimed in claim 2 wherein compound $a$ is 3-isopropyl-2,1,3-benzothiadiazinone-(4)-2,2-dioxide or its salt and compound $b$ is 3,5-dibromo-4-hydroxybenzonitrile, 3,5-diiodo-4-hydroxybenzonitrile, or 3,5-dibromo-4-octanoyloxybenzonitrile.

4. A herbicide composition as claimed in claim 1 wherein compound $a$ is 3-isopropyl-2,1,3-benzothiadiazinone-(4)-2,2-dioxide and compound $b$ is 3,5-dibromo-4-hydroxybenzonitrile.

5. A herbicide composition as claimed in claim 3 wherein compound *a* is 3-isopropyl-2,1,3-benzothiadiazinone-(4)-2,2-dioxide and compound *b* is 3,5-diiodo-4-hydroxybenzonitrile.

6. A herbicide composition as claimed in claim 3 wherein compound *a* is 3-isopropyl-2,1,3-benzothiadiazinone-(4)-2,2-dioxide and compound *b* is 3,5-dibromo-4-octanoyloxybenzonitrile.

* * * * *